US00PP12360P2

(12) United States Plant Patent
Tucker

(10) Patent No.: US PP12,360 P2
(45) Date of Patent: Jan. 22, 2002

(54) MINIATURE ROSE PLANT NAMED 'TUCKTOMMY'

(76) Inventor: Robert T. Tucker, 9404 Hunting Hills Dr., Franklin, TN (US) 37607

( * ) Notice: Subject to any disclaimer, the term of this patent is extended or adjusted under 35 U.S.C. 154(b) by 0 days.

(21) Appl. No.: 09/477,639

(22) Filed: Jan. 5, 2000

(51) Int. Cl.[7] ..... A01H 5/00

(52) U.S. Cl. ..... Plt./118

(58) Field of Search ..... Plt./116, 118, 119, Plt./125, 126

*Primary Examiner*—Howard J. Locker

(57) ABSTRACT

This invention relates to a new and distinct variety of miniature rose plant primarily identified by its medium yellow buds and flowers, garden rose form and medium green matte foliage.

1 Drawing Sheet

The present invention relates to a new and distinct variety of hardy, dwarf, bush type rose plant of the miniature class; the variety being primarily characterized—as to novelty—by buds and flowers of a uniform medium yellow color which generally are of garden form.

The variety is further characterized by:

An abundance of bloom, with flowers often borne singly and also several to the stem in loose clusters.

No fragrance.

A plant which is vigorous, bushy, round shape with medium growth habit and medium green matte foliage.

A plant which has an average height of 14–20 inches, and can easily be maintained at lesser height by occasional trimming.

A plant which grows and blooms satisfactorily both in the greenhouse and outdoors; is good for growing in pots; and provides excellent garden decoration as well as cut flowers.

The present variety of miniature rose was originated by me in my hybridizing garden located at Franklin, Tenn. under conditions of careful control and observation, as a cross between Rise 'n Shine (U.S. Plant Pat. No. 4,231) as the seed parent and the miniature rose, Captivation (not patented) as the pollen parent.

Subsequent to origination of the variety, I successfully asexually reproduced it at my hybridizing garden, located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The Royal Horticultural Society Colour Chart, except where common terms of color definition are employed.

Class: Miniature. Variety identification: TUCktommy (Commercial synonym: Little Tommy Tucker).

FLOWER

Observations made from specimens grown in a garden environment at Franklin, Tenn. in May 1996 through September 1999.

Blooming habit: Continuous.

Bud:

*Size.*—½ to ¾ inch long when the petals start to unfurl.

*Form.*—The bud form is oval shaped and of medium length.

*Color.*—When the sepals first divide, bud color is Yellow Orange Group 21C.

*Sepals.*—Color: Medium green. Surface texture: Mostly smooth.

*Peduncle.*—Length: Short to medium. ½ to 1 inch. Surface: Smooth. Strength: Stiff. Color: Light green.

Bloom:

*Size.*—Medium for a dwarf-type rose; Average open size is 2.0 inches across.

*Borne.*—Singly and sometimes in clusters of 2 to 6 flowers.

*Stems.*—Small and strong.

*Form.*—High centered only at first opening; Reflexed petals; Opens quickly. When fully open stamens show.

*Petalage.*—Double; Number of petals under normal conditions: 15–25. Arranged regularly plus some small petaloids. Petals have average substance.

*Color.*—The petals' upper and lower sides begin at Yellow Orange Group 21 C and fade over a Period of days to Yellow Orange Group 19D.

*Variegations.*—None.

*Discoloration.*—The general tonality at the end of the first day: No change. At the end of the third day: Some fading. At the end of the bloom cycle fades to light yellow.

*Fragrance.*—None.

Reproductive parts:

*Anthers.*—Size: Medium; Quantity: Many; Color: Yellow; Arrangement: Regular around styles.

*Filaments.*—Varying length, short to medium long, yellow.

*Pollen.*—Quantity: Very heavy; Color: Golden yellow.

*Styles.*—Color: Yellow.

*Stigmas.*—Color: Light yellow to Light green.

*Ovaries.*—All enclosed in calyx.

*Hips.*—Sets Hips readily.

*Seeds.*—Small to medium size and fairly regular (round) for dwarf type plant.

Growth:

*Habit.*—Dwarf; mostly upright; vigorous to 20 inches.

Foliage:

*Leaflets.*—Number on normal mid-stem leaves: 5 or 7.

*Size.*—Medium; Leaflets vary in length from ½ to 2 inches.

*Quantity.*—Abundant.

*Color.*—New foliage: Reddish Purple changing to Medium green.

*Old foliage.*—Upper surface: Green Group 137A. Lower surface: Green Group 138B.

Leaflets:

*Shape.*—Pointed oval.

*Texture.*—Some; Slightly smooth; dull/matte.

*Edge.*—Serrated.

*Serration.*—Single, small.

*Petiole rachis.*—Smooth and light green. Some reddish coloration on new growth.

*Petiole underside.*—Smooth and Light Green.

*Stipules.*—Medium to short length (¼ to ½ inch)

Wood:

*New wood.*—Color: Reddish but turns medium green very quickly. Bark smooth.

*Old wood.*—Color: Medium green; Bark smooth.

Prickles:

*Quantity.*—Average Number.

*Form.*—Varying sizes from small prickles to medium thorns; Medium thorn size (¼ to ½ inch); Prickles project straight from stem and some hooked slightly down.

The miniature rose plant and its flowers as herein described may vary in slight detail due to climatic, soil and cultural conditions under which the variety may be grown; the present description being of the variety as grown at Franklin, Tenn.

The following is claimed:

1. A new and distinct variety of miniature rose plant of hardy, dwarf, upright habit, substantially as illustrated and described, characterized by buds and flowers of garden form, essentially medium yellow in color, with reverse same, and further characterized by a plant of bushy shape, vigorous, with the main stems and shoots being moderately thorny, the said plant being easy to propagate from cuttings, with an abundance of flowers borne singly or several to a stem.

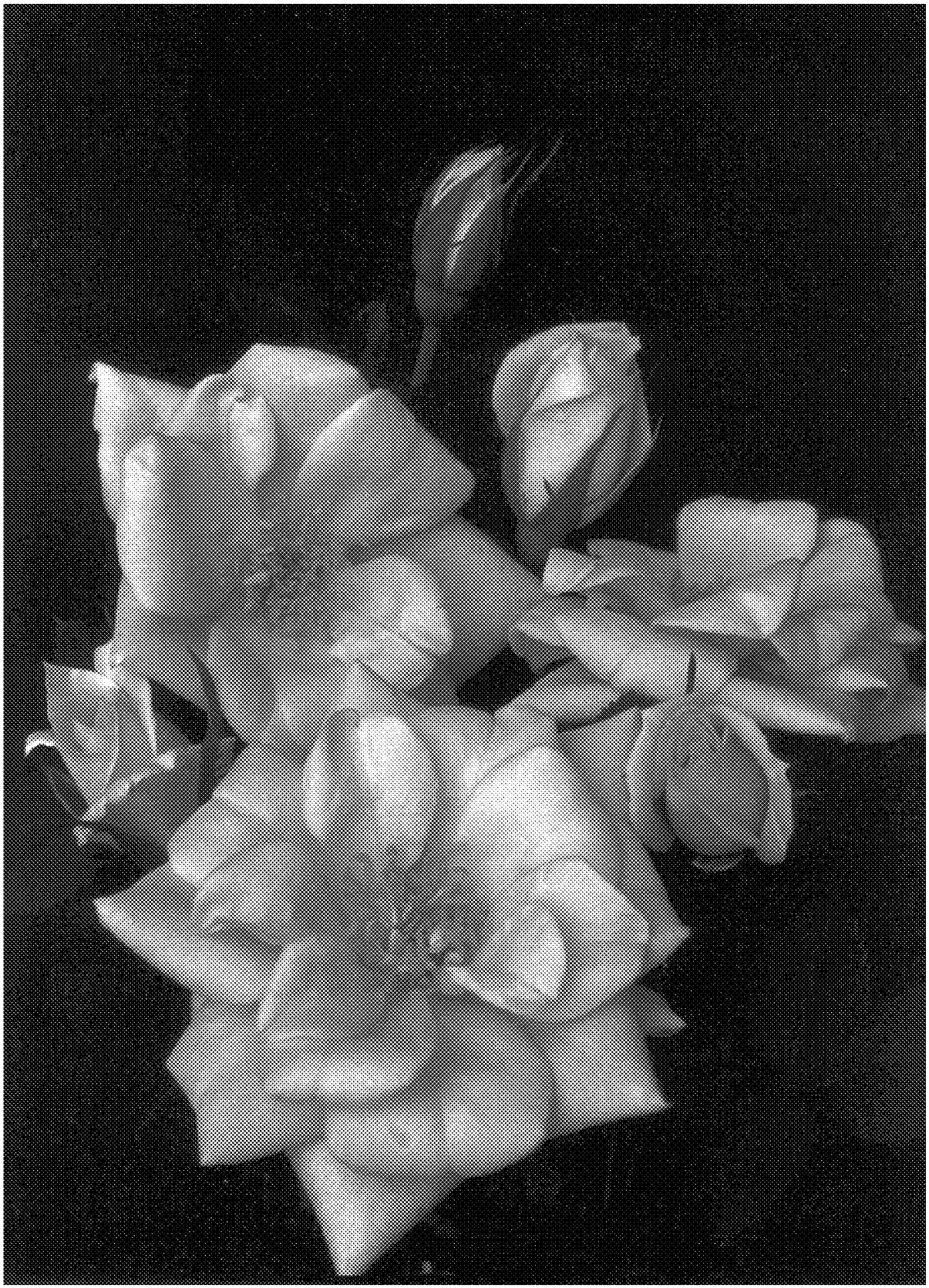

* * * * *